(12) United States Patent
Kaji et al.

(10) Patent No.: US 6,881,695 B2
(45) Date of Patent: Apr. 19, 2005

(54) OLEFIN POLYMERIZATION CATALYST AND METHOD FOR PRODUCING MODIFIED METHYLALUMINOXANE FOR USE AS OLEFIN POLYMERIZATION CATALYST

(75) Inventors: Eiichi Kaji, Yamaguchi (JP); Kouji Toyota, Yamaguchi (JP); Toshihiro Takasugi, Yamaguchi (JP); Hideki Kanazawa, Yamaguchi (JP)

(73) Assignee: Tosoh Finechem Corporation, Yamaguchi (JP)

( * ) Notice: Subject to any disclaimer, the term of this patent is extended or adjusted under 35 U.S.C. 154(b) by 0 days.

(21) Appl. No.: 10/408,267

(22) Filed: Apr. 8, 2003

(65) Prior Publication Data

US 2003/0195307 A1 Oct. 16, 2003

(30) Foreign Application Priority Data

Apr. 8, 2002 (JP) .................................... 2002-104734
Oct. 9, 2002 (JP) .................................... 2002-295882

(51) Int. Cl.$^7$ ............................ C08F 4/02; B01J 37/00; B01J 31/00
(52) U.S. Cl. ................... 502/111; 502/103; 502/117; 502/120; 502/152; 526/124.1; 526/160; 526/943; 556/178
(58) Field of Search ............................. 526/124.1, 160, 526/943; 502/103, 111, 117, 120, 152; 556/178

(56) References Cited

U.S. PATENT DOCUMENTS 4,937,217 A * 6/1990 Chang ..................... 502/111
5,006,500 A * 4/1991 Chang ..................... 502/107
5,041,584 A * 8/1991 Crapo et al. .............. 556/179
5,157,008 A * 10/1992 Sangokoya et al. ........ 502/111

FOREIGN PATENT DOCUMENTS

| EP | 0 324 856 | 7/1989 |
| EP | 0 372 617 | 6/1990 |
| EP | 0 393 358 | 10/1990 |
| JP | 4-46906 A | * 2/1992 |
| WO | 99/15534 | 4/1999 |

OTHER PUBLICATIONS

Database CA Online, Chemical Abstracts Service, Database accession No. 115:1600019, XP002248182 (Abstract of JP 03–103407 A, Apr. 30, 1991).
Database WPI, Section Ch, Week 199213, Derwent Publications Ltd., London, GB, AN 1992–102341, XP002248183 (Abstract of JP 04 046906 A, Feb. 17, 1992).

* cited by examiner

Primary Examiner—Ling-Siu Choi
(74) Attorney, Agent, or Firm—Wenderoth, Lind & Ponack, L.L.P.

(57) ABSTRACT

An olefin polymerization catalyst is provided which makes use of a modified methylaluminoxane and thus stably exhibits an activity equivalent to, or higher than, the activity achieved by polymethylaluminoxane. Specifically, the olefin polymerization catalyst is in the form of a modified methylaluminoxane preparation prepared from: an organoaluminum compound represented by the following general formula (I):

$$R^1_m AlX_{3-m} \qquad (I)$$

wherein $R^1$ represents a straight-chained or branched hydrocarbon group selected from the group consisting of alkyl, alkenyl, and aryl groups having 2 to 20 carbon atoms; X represents a hydrogen atom, halogen atom, alkoxy group, or allyloxy group; and $0 < m \leq 3$; and trimethyl aluminum, wherein the mole fraction of methyl group of the aluminoxane unit with respect to the total number of moles of the hydrocarbon group having 2 to 20 carbon atoms and methyl group present in the modified methylaluminoxane preparation is 65 mol % or greater.

2 Claims, 1 Drawing Sheet

Fig. 1

OLEFIN POLYMERIZATION CATALYST AND METHOD FOR PRODUCING MODIFIED METHYLALUMINOXANE FOR USE AS OLEFIN POLYMERIZATION CATALYST

BACKGROUND OF THE INVENTION

1. Field of the Invention

The present invention relates to a catalyst for olefin polymerization that makes use of a novel modified methylaluminoxane preparation and to a method for producing such a modified methylaluminoxane preparation for use as the olefin polymerization catalyst, as well as to a method for carrying out olefin polymerization involving the use of the novel methylaluminoxane preparation as a polymerization catalyst component.

2. Description of the Related Art

The following patent publications and articles are incorporated herein by reference in their entirety: Japanese Patent Laid-Open Publications No. Sho 58-19309; Sho 60-35005; Sho 62-234009; Sho 63-234009; Sho 64-66214; Hei 1-207355; 2000-119278; 2000-119279; 2000-119280; Sho 60-260602; Sho 63-89506; Sho 63-178108; Hei 1-315407; Hei 2-22308; Sho 60-35006; Sho 60-35007; Sho 60-35008; Sho 61-108610 and Sho 61-296008; *Macromolecules*, 32, 9078 (1999); *Journal of American Chemical Society* (J. Am. Chem. Soc.) 118, 11664 (1996); and *Organometallics* 18, 65, (1999).

Aluminoxanes are condensation products generally prepared by partial hydrolysis of organoaluminum compounds and are known as a useful co-catalyst for the production of olefin polymers that can efficiently activate a transitional metal compound, a primary catalyst of the reaction. It is widely known that polymethylaluminoxane, which is made by using trimethyl aluminum as the organoaluminum material, is a particularly effective co-catalyst. Examples of these compounds are described in, for example, Japanese Patent Laid-Open Publications No. Sho 58-19309; Sho 60-35005; Sho 62-234009; Sho 63-234009; Sho 64-66214; and Hei 1-207355.

Modified aluminoxanes having two or more different types of alkyl groups have also been proposed: One type of modified aluminoxane disclosed in Japanese Patent Laid-Open Publications No. 2000-119278, 2000-119279 and 2000-119280 is produced by first mixing trimethyl aluminum with tetraalkyldialuminoxane that has alkyls with 2 or more carbon atoms and subsequently carrying out hydrolysis. The modified methylaluminoxanes synthesized using these techniques are soluble not only in aromatic hydrocarbon solvents but also in aliphatic hydrocarbon solvents and are, therefore, widely used in the production of olefin polymers for use in food products, for which use of aromatic solvents is restricted. Also, these modified methylaluminoxanes are highly stable while in storage. In addition, these compounds are synthesized through a mild reaction that can be readily controlled. However, the modified methylaluminoxanes made by the above-described techniques exhibit a lower activity than polymethylaminoxane and thus need to be improved.

Different techniques for solubilizing polymethylaluminoxane in aliphatic hydrocarbon solvents have been proposed in, for example, Japanese Patent Laid-Open Publications No. Sho 60-260602, Sho 63-89506, Sho 63-178108, Hei 1-315407, and Hei 2-22308. In a typical approach, polymethylaluminoxane produced in an aromatic hydrocarbon solvent is exposed to an alkylaluminum other than trimethylaluminum so as to increase the solubility of polymethylaluminoxane in the solvent. In this technique, however, when it is desired to replace the aromatic hydrocarbon solvent with an aliphatic hydrocarbon solvent, the aromatic hydrocarbon solvent is removed by taking advantage of its relatively high boiling point in the distillation under reduced pressure or other proper processes. In practice, as much as several percent by weight of the aromatic hydrocarbon solvent inevitably remains after the solvent replacement. Though effective in some cases at laboratory level, such a solvent replacement process is highly impractical for use in industrial applications.

A particular type of solid catalyst that is provided in the form of silica, alumina, magnesium chloride and other solid carriers carrying a transitional metal compound along with an aluminoxane has been in use. Several methods have been proposed concerning the use of such a solid catalyst component in the suspension polymerization or the gas phase polymerization. Examples of such methods are disclosed in, for example, Japanese Patent Laid-Open Publications No. Sho 60-260602, Sho 63-89506, Sho 63-178108, Hei 1-315407, and Hei 2-22308.

In most of the known examples mentioned above, polymethylaluminoxane is used as the aluminoxane in preparing the solid catalyst. Since trimethyl aluminum, the principal material of polymethylaluminoxane, is significantly more reactive than the other members of organoaluminum compound, it is difficult to control partial hydrolysis, and the insoluble, aluminum hydroxide-like inorganic aluminum compound resulting from the local hydrolysis can lead to a decrease in the yield as measured on the basis of aluminum atom. In addition, polymethylaluminoxane tends to become less soluble in the solvent as it undergoes association process. As a result, insoluble product is often formed, affecting the stability of polymethylaluminoxane during storage. For these reasons, there has been a large demand for the development of a novel modified methylaluminoxane that maximizes the yield as measured on the basis of aluminum atom while providing improved storage stability.

Since previously known modified methylaluminoxanes, when used in a catalyst using silica or other carriers, could only impart significantly lower activity to the solid catalyst than is achieved by polymethylaluminoxane, they have never been actively used in carrier catalysts. The cause of this low activity is believed to be that the amount of the alkylaluminum compound with alkyl group having 2 or more carbon atoms that was present in the modified methylaluminoxane and/or the amount of the modified methylaluminoxane with alkyl group having 2 or more carbon atoms were not suitable for the preparation of the carrier catalyst.

Recently, new catalyst systems for olefin polymerization were found in which a modified methylaluminoxane exhibits co-catalyst activity that is equivalent to, or even higher than, that of polymethylaluminoxane. As a result, application of modified methylaluminoxanes as co-catalyst for polymerization has attracted much attention. Examples of such system are described in *Macromolecules*, 32, 9078 (1999); *Journal of American Chemical Society* 118, 11664 (1996); and *Organometallics* 18, 65, (1999).

SUMMARY OF THE INVENTION

Accordingly, it is an objective of the present invention to provide a novel catalyst for olefin polymerization that makes use of a modified methylaluminoxane and thus stably exhibits an activity equivalent to, or higher than, the activity achieved by using polymethylaluminoxane.

In the search for a way to overcome the above-identified drawbacks of the prior art, the present inventors have discovered that the foregoing objective of the invention can be attained by using a specific type of modified methylaluminoxane obtained through a reaction of two or more different organoaluminum compounds with a condensation agent, such as water, to serve as an oxygen source. The discovery ultimately led the present inventors to complete the present invention.

Thus, the concept of the present invention is made up of the following aspects:

(1) an olefin polymerization catalyst in the form of a modified methylaluminoxane preparation prepared from:

an organoaluminum compound represented by the following general formula (I):

$$R^1_m AlX_{3-m} \qquad (I)$$

wherein $R^1$ represents a straight-chained or branched hydrocarbon group selected from the group consisting of alkyl, alkenyl, and aryl groups having 2 to 20 carbon atoms; X represents a hydrogen atom, halogen atom, alkoxy group, or allyloxy group; and $0 < m \leq 3$; and trimethyl aluminum, wherein the mole fraction of methyl group of the aluminoxane unit with respect to the total number of moles of the hydrocarbon group having 2 to 20 carbon atoms and methyl group present in the modified methylaluminoxane preparation is 65 mol % or greater.

(2) The olefin polymerization catalyst as described in (1) above, wherein the mole fraction of the hydrocarbon group with 2 to 20 carbon atoms that belongs to the aluminoxane unit with respect to the total number of moles of the hydrocarbon group with 2 to 20 carbon atoms and methyl group present in the modified methylaluminoxane preparation is 15 mol % or less.

(3) The olefin polymerization catalyst as described in (1) or (2) above, wherein the organoaluminum compound of the general formula (I) is at least one selected from the group consisting of triisobutylaluminum, tri-n-hexylaluminum, and tri-n-octylaluminum.

(4) The olefin polymerization catalyst, wherein the modified methylaluminoxane as described in any one of (1) to (3) above is used in a solid catalyst serving as the olefin polymerization catalyst, the solid catalyst being formed from fine particle carrier, and a transitional metal compound and the modified methylaluminoxane preparation carried by the fine particle carrier.

(5) The olefin polymerization catalyst as described in (4) above, wherein the transitional metal compound is a compound represented by the following general formula (II):

$$MR^2R^3R^4R^5 \qquad (II)$$

wherein M represents a transitional metal element; and $R^2$, $R^3$, $R^4$ and $R^5$ together form any organic group having a cycloalkadienyl skeleton or are each independently selected from the group consisting of an organic group having a cycloalkadienyl skeleton, alkyl group, alkoxy group, aryloxy group, alkylsilyl group, alkylamide group, alkylimide group, alkylamino group, alkylimino group, and halogen atom.

(6) A method for producing the modified methylaluminoxane preparation as described in any one of (1) to (4) above, comprising the steps of:

hydrolyzing the organoaluminum compound represented by the following general formula (I):

$$R^1_m AlX_{3-m} \qquad (I)$$

wherein $R^1$ represents a straight-chained or branched hydrocarbon group selected from the group consisting of alkyl, alkenyl, and aryl groups having 2 to 20 carbon atoms; X represents a hydrogen atom, halogen atom, alkoxy group, or allyloxy group; and $0 < m \leq 3$;

adding trimethyl aluminum to carry out hydrolysis; and repeating the step of adding trimethyl aluminum as many times as necessary.

(7) A method for producing the olefin polymerization catalyst as described in (5) above, comprising the steps of:

exposing the fine particle carrier to the modified methyl aluminoxane preparation; and subsequently exposing the fine particle carrier to the transitional metal compound.

(8) A method for olefin polymerization making use of either a catalyst system comprising the transitional metal compound and the modified methylaluminoxane as described in (1) to (3) above or the solid catalyst as described in (5) above.

In summary, the present invention concerns a catalyst component comprising:

an olefin polymerization catalyst in the form of a modified methylaluminoxane preparation prepared from:

an organoaluminum compound represented by the following general formula (I):

$$R^1_m AlX_{3-m} \qquad (I)$$

wherein $R^1$ represents a straight-chained or branched hydrocarbon group selected from the group consisting of alkyl, alkenyl, and aryl groups having 2 to 20 carbon atoms; X represents a hydrogen atom, halogen atom, alkoxy group, or allyloxy group; and $0 < m \leq 3$; and trimethyl aluminum, wherein the mole fraction of methyl group of the aluminoxane unit with respect to the total number of moles of the hydrocarbon group having 2 to 20 carbon atoms and methyl group present in the modified methylaluminoxane preparation is 65 mol % or greater; and any transitional metal compound. The present invention also concerns an olefin polymerization solid catalyst in the form of the catalyst component carried by a solid carrier.

DETAILED DESCRIPTION OF THE PREFERRED EMBODIMENTS

The present invention will now be described in detail with reference to some examples, which are not exhaustive but only illustrative.

A modified methylaluminoxane in accordance with the present invention is a composition (which herein may be referred to as 'modified methylaluminoxane preparation') that contains, in addition to a modified methylaluminoxane of interest, unreacted materials, that is, the organoaluminum compound of the general formula (1) and/or trimethyl aluminum.

Accordingly, "$C_{2-20}$ hydrocarbon group present in the modified methyl aluminoxane preparation" as described in the paragraph (1) above includes both $C_{2-20}$ hydrocarbon group within the molecules of the modified methylaluminoxane and $C_{2-20}$ hydrocarbon group within the molecules of the organoaluminum compound that remains unreacted in the modified methyl aluminoxane preparation. Similarly, "methyl group" as described in the paragraph (1) above, which accounts for part of the total number of moles, includes both methyl group in the aluminoxane units within the molecules of the modified methylaluminoxane and methyl group within the molecules of the trimethyl aluminum that remains unreacted in the modified methylaluminoxane preparation.

The modified methylaluminoxane in accordance with the present invention is deemed to be a compound consisting of unit represented by the following general formula (III):

$$—[(R^1)AlO]_n—[(Me)AlO]_p—\qquad (III)$$

wherein $R^1$ is the same as defined above; and n and p are each individually an integer from 1 to 60. The modified methylaluminoxane of the present invention may have either a chain-like structure or a ring structure, provided that it includes the above units. The two structural units of the modified methylaluminoxane, —$(R^1)$AlO— and —(Me)AlO—, may be joined to one another either in blocks of homopolymers as shown by the general formula (III), or in a random fashion, or in combinations of homopolymer blocks and random sequences. It should be understood that $R^1$ in the general formula (III) does not necessarily indicate a single type of hydrocarbon group but may indicate a mixture of more than one type of the hydrocarbon groups specified above.

Specifically, examples of $R^1$ in the general formula (III) are alkyl groups such as ethyl, propyl, n-butyl, isobutyl, t-butyl, amyl, isoamyl, n-hexyl, isohexyl, n-octyl, and isooctyl, and aryl groups such as phenyl and tolyl. Of these, n-butyl, isobutyl, n-hexyl, n-octyl, and isooctyl are particularly preferred.

The organoaluminum compound for use in the production of the modified methylaluminoxane preparation of the present invention can be expressed by the general formula (I):

$$R^1_m AlX_{3-m} \qquad (I)$$

wherein $R^1$ and m are the same as defined above.

Specifically, examples of $R^1$ in the general formula (I) are alkyl groups such as ethyl, propyl, n-butyl, isobutyl, t-butyl, amyl, isoamyl, n-hexyl, isohexyl, n-octyl, and isooctyl, and aryl groups such as phenyl and tolyl. Examples of X include halogen atoms such as fluorine, chlorine, bromine and iodine, and alkoxy groups such as methoxy and ethoxy, and allyloxy groups such as phenoxy.

Specific examples of such an organoaluminum compound include alkyl aluminum such as trimethyl aluminum, tripropyl aluminum, tri-n-butyl aluminum, triisobutyl aluminum, tri-n-hexyl aluminum and tri-n-octyl aluminum; triaryl aluminum such as triphenyl aluminum and tritolyl aluminum; and halogen-containing alkyl aluminum such as dimethyl aluminum chloride and diethyl aluminum chloride. These organoalkylaluminums may be used either individually or in combination to obtain desired modified methylaluminoxane preparations. The most preferred organoaluminum compounds and combinations thereof in preparing the modified methylaluminoxane preparation are trimethyl aluminum and trialkyl aluminum, specifically, trimethyl aluminum and triisobutyl aluminum, tri-n-hexyl aluminum, or tri-n-octyl aluminum and combinations thereof.

Conventional modified methylaluminoxane preparations are generally characterized by the molar ratio of methyl group to $C_{2-20}$ hydrocarbon group in the preparations. In general, polymethylaluminoxane made from trimethyl aluminum alone exhibits high co-catalyst activity when used as a co-catalyst to help metallocene or other catalysts catalyze olefin polymerization, whereas aluminoxane of the general formula (I), which is made from an organoaluminum compound other than trimethyl aluminum, exhibits little co-catalyst activity except when it is used in certain catalyst systems such as chromium complex. For this reason, it can be inferred that a modified methylaluminoxane preparation tends to show a higher co-catalyst activity as the molar ratio of methyl group to $C_{2-20}$ hydrocarbon atoms in the preparation is increased. However, this rule does not always hold since the modified methyl aluminoxane preparation contains, in addition to the desired modified methylaluminoxane, unreacted organoaluminum compound of the general formula (I) and trimethyl aluminum and the proportion of the unreacted materials tends to vary from time to time. In light of this, the present inventors have found that the mole fraction of methyl group of the aluminoxane unit with respect to the total number of moles of $C_{2-20}$ hydrocarbon group and methyl group in the modified methylaluminoxane preparation provides a better measure for assessing the co-catalyst activity of the modified methylaluminoxane preparation than the molar ratio of methyl group to $C_{2-20}$ hydrocarbon group in the modified methylaluminoxane preparation.

Furthermore, the present inventors assessed modified methylaluminoxane preparations prepared under different conditions using the above-described measure and, at the same time, made a comparison of the co-catalyst activity in a homogenous system among different modified methylaluminoxane preparations, as well as of the polymerization activity among different solid catalyst components prepared in the form of a solid carrier carrying each of the modified methylaluminoxanes and a transitional metal catalyst. As a result, it has proven that when the aforementioned new measure for assessing the co-catalyst activity of the modified methylaluminoxane preparation has a value of 65 mol % or higher, the modified methylaluminoxane preparation exhibits a specific activity that is higher than the specific activity of any of conventional modified methylaluminoxanes and is equivalent to, or higher than, the specific activity of polymethylaluminoxane.

If the above-described measure for assessing the co-catalyst activity of the modified methylaluminoxane preparation has a value less than 65 mol %, then the co-catalyst activity of the modified methylaluminoxane preparation does not exceed the co-catalyst activity achieved by commercially available modified methylaluminoxanes.

In general, trimethyl aluminum itself hardly shows co-catalyst activity when used in the olefin polymerization in which a metallocene catalyst or the like is used as the catalyst, as does the organoaluminum compound of general formula (I) having $C_{2-20}$ hydrocarbon group. The co-catalyst activity in olefin polymerization is assessed with the ratio of the number of moles of aluminum in the co-catalyst to the number of moles of the metallocene catalyst adjusted to a predetermined value. Thus, a given modified methylaluminoxane preparation is considered more favorable if it contains a larger proportion of aluminum belonging to the polymethylaluminoxane component, the component that enhances the co-catalyst activity. In other words, less organoaluminum component is more favored. Similarly, when the modified methylaluminoxane preparation is carried by a carrier, it is more desirable if the proportion of aluminum belonging to the polymethylaluminoxane component is maximized and, thus, the proportion of the organoaluminum component is minimized.

Also, when it is desired to prepare high-molecular weight polymers, it is preferred that the amounts of these organoaluminum compounds be minimized because of their ability as a polymerization chain transfer agent.

For these reasons, the present inventors have found that the modified methylaluminoxane as defined in the paragraph (1) above can be used either in combination with the transitional metal compound or in the form of a solid catalyst to elicit a high activity in olefin polymerization.

Also, if the mole fraction of $C_{2-20}$ hydrocarbon belonging to the aluminoxane unit with respect to the total number of moles of methyl group and $C_{2-20}$ hydrocarbon in the modified methylaluminoxane preparation exceeds 15 mol %, the modified methylaluminoxane preparation does not exhibit co-catalyst activity as high as that of commercially available modified methylaluminoxane, resulting in reduced molecular weights of the polymer products.

The modified methylaluminoxane of the present invention can be used with any inert hydrocarbon solvent. The hydrocarbon includes saturated aliphatic hydrocarbons such as n-pentane, n-hexane, n-heptane, n-octane, isooctane, and purified kerosines; cyclic aliphatic hydrocarbons such as cyclopentane, cyclohexane, methylcyclohexane, ethylcyclohexane, and cycloheptane; and aromatic hydrocarbons such as benzene, toluene, ethylbenzene, o-xylene, m-xylene, and p-xylene. Of these compounds, n-hexane, n-heptane, n-octane, cyclohexane, methylcyclohexane, and toluene are particularly preferred.

The modified methylaluminoxane preparation of the present invention may be synthesized using any known technique. One typical technique is as follows: a predetermined amount of the organoaluminum compound of the general formula (I) is first hydrolyzed, and trimethyl aluminum is subsequently introduced for further hydrolysis. While the modified methylaluminoxane preparation produced in this manner does not require any particular post-reaction treatment, solvent and other low boiling point compounds such as residual organoaluminum compound may be distilled out under reduced pressure, if necessary, for the purpose of for example adjusting the concentration of aluminum. Further, when necessary, the reaction system may be heated at some point during the course of the reaction.

Water may be used in hydrolysis in various forms including water droplets, water vapor, water contained in crystallized inorganic compounds, and water diluted with nitrogen or other inert gases or inert hydrocarbon solvents.

The molar ratio of trimethyl aluminum to the organoaluminum compound of the general formula (I) for use in the synthesis of the modified methylaluminoxane preparation may be adjusted to any ratio ranging from 0.5:1 to 30:1. Though it depends on the type of the organoaluminum compound of the general formula (I) to serve as a modifier, the molar ratio is preferably adjusted to a range of 2:1 to 20:1. In this manner, modified methylaluminoxane preparation is obtained that can provide high yield as measured based on aluminum atom and co-catalyst activity in a well-balanced manner.

The molar ratio of water to serve as a condensation agent to the organoaluminum compound of the general formula (I) is preferably adjusted to a range of 0.1:1 to 1.5:1 depending on the chain length of hydrocarbon group in the organoaluminum compound of the general formula (I).

The reaction is carried out at temperatures of −50 to 50° C. and preferably at temperatures of −30 to 30° C.

While the solution of the modified methylaluminoxane preparation resulting after completion of the reaction is preferably kept stirred and aged for a prolonged time while the reaction temperature is maintained, it may also be heat-aged at a lower temperature than the boiling point of the reaction solvent. The concentration of the modified methylaluminoxane in the inert hydrocarbon solvent is preferably in the range of 1 to 40% by weight, more preferably 5 to 25% by weight, and still more preferably 5 to 20% by weight.

The modified methylaluminoxane products generally contain, along with trimethyl aluminum, residual organoaluminum compound of the general formula (I) that has not been hydrolyzed, as is the case with the modified methyl aluminoxane preparation of the present invention. When, for example, isobutyl is the hydrocarbon group, the molar ratio of methyl group/isobutyl group (written simply as Me/iBu, hereinafter) in the modified methylaluminoxane preparation can be determined by the quantitative gas chromatography analysis of the components generated upon hydrolysis of the modified methylaluminoxane preparation.

The modified methylaluminoxane preparation in accordance with the present invention is characterized by the respective mole fractions of methyl group belonging to the unreacted trimethyl aluminum and methyl group belonging to the aluminoxane unit (written as Me(TMAL) and Me(modified methylaluminoxane), respectively), in conjunction with the respective mole fractions of hydrocarbon group with 2 to 20 carbon atoms belonging to the residual organoaluminum compound and hydrocarbon group with 2 or more carbon atoms belonging to the aluminoxane unit (written as R(AlR₃) and R(modified methylaluminoxane), respectively).

Figure 1:
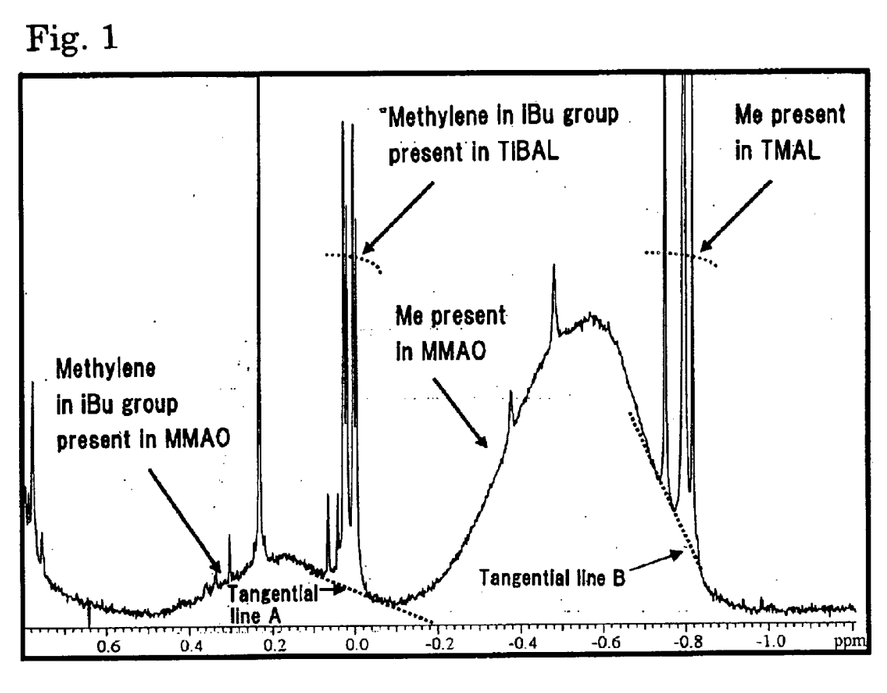
FIGURE is a diagram showing the results of $^1$H-NMR spectroscopy of a modified methylaluminoxane preparation obtained in accordance with the present invention.

The mole fraction of each component in the modified methylaluminoxane can be determined by the ¹H-NMR analysis of modified methylaluminoxane preparation from the proportions of the areas corresponding to the respective components. For example, when trimethyl aluminum (TMAL) and triisobutyl aluminum (TIBAL) are used to serve as two different organoaluminum compounds, the mole fractions of Me(modified methylaluminoxane), Me(TMAL), iBu(modified methylaluminoxane) and iBu (TIBAL) can be determined in the following manner:

First, the modified methylaluminoxane preparation was subjected to ¹H-NMR analysis using $d_8$-THF as a deuterized solvent. ¹H-NMR analysis was performed at a temperature of 24° C. on a 300 MHz Gemini 2000 NMR manufactured by VARIAN TECHNOLOGIES JAPAN Ltd. The results of ¹H-NMR spectroscopy is shown in FIG. 1.

(i) The total area under the peaks indicating methylene groups and Me groups of the modified methylaluminoxane that appear in the range from about 0.5 ppm to about −1 ppm is determined by integration and is referred to as I(modified methylaluminoxane).

(ii) The area under the peaks that appear near 0 ppm and indicate methylene group of TIBAL and above the tangential line A is determined by integration and is referred to as I(TIBAL-iBu). Similarly, the area under the tangential line A corresponding to methylene group of the modified methylaluminoxane is determined by integration and is referred to as I(modified methylaluminoxane-iBu).

(iii) As in (ii) above, the area under the peaks that appear near −0.8 ppm and indicate Me group of TMAL and above the tangential line B is determined by integration and is referred to as I(TMAL-Me). Similarly, the area under the tangential line B corresponding to Me group of modified methylaluminoxane is determined by integration and is referred to as I(modified methylaluminoxane-Me).

(iv) The areas obtained in (ii) and (iii) are divided by the numbers of protons of the respective functional groups and are then normalized to give the mole fractions of Me(modified methylaluminoxane), Me(TMAL), iBu (modified methylaluminoxane), and iBu(TIBAL), respectively.

Integration of the peaks can be conveniently performed by using curve fitting or baseline correction.

The transitional metal compound that is used in conjunction with the modified methylaluminoxane preparation of the present invention in the preparation of a polymerization catalyst may be any known catalyst for olefin polymerization. Such transitional metal compounds include those represented by the following general formula (II):

$$MR^2R^3R^4R^5 \tag{II}$$

wherein M represents a transitional metal element; and $R^2$, $R^3$, $R^4$ and $R^5$ together form any organic group having a cycloalkadienyl skeleton or are each independently selected from the group consisting of an organic group having a cycloalkadienyl skeleton, alkyl group, alkoxy group, aryloxy group, alkylsilyl group, alkylamide group, alkylimide group, alkylamino group, alkylimino group, and halogen atom.

Specifically, M in the general formula (ii) may be titanium, zirconium, hafnium, chromium, vanadium, manganese, iron, cobalt, nickel, and palladium. Of these, titanium, zirconium, chromium, iron, and nickel are preferred.

Preferably, the transitional metal compound in the general formula (II) is a metallocene compound that includes one or two ligands with cycloalkadienyl skeleton. Examples of the ligand with cycloalkadienyl skeleton include alkyl-substituted cyclopentadienyl groups such as cyclopentadienyl group, methylcyclopentadienyl group, ethylcyclopentadienyl group, butylcyclopentadienyl group, dimethylcyclopentadienyl group, and pentamethylcyclopentadienyl group, indenyl group, and fluorenyl group. The cycloalkadienyl groups may be crosslinked with divalent substituted alkylene or substituted silylene.

The ligand other than those forming cycloalkadienyl skeleton may be a hydrocarbon group with 1 to 20 carbon atoms, alkoxy group, aryloxy group, alkylsilyl group, amino group, imino group, halogen atom or hydrogen atom. Examples of the hydrocarbon group having 1 to 20 carbon atoms include alkyl group, cycloalkyl group, aryl group, and aralkyl group. Specifically, the alkyl group includes methyl group, ethyl group, propyl group, isopropyl group, and butyl group. The cycloalkyl group includes cyclopentyl group and cyclohexyl group. The aryl group includes phenyl group and tolyl group. The aralkyl group includes benzyl group. The alkoxy group includes methoxy group, ethoxy group, and butoxy group. The aryloxy group includes phenoxy group. These functional groups may include halogen atoms or other substituents. The alkylsilyl group includes trimethylsilyl group and triethylsilyl group. The halogen includes fluorine, chlorine, bromine and iodine.

When M in the general formula (II) represents zirconium, specific examples of the transitional metal compound with ligands forming cycloalkadienyl skeleton include bis(cyclopentadienyl)zirconium monochloride monohydride, bis(cyclopentadienyl)zirconium monobromide monohydride, bis(cyclopentadienyl)methylzirconium hydride, bis(cyclopentadienyl)ethylzirconium hydride, bis(cyclopentadienyl)phenylzirconium hydride, bis(cyclopentadienyl)benzylzirconium hydride, bis(cyclopentadienyl)neopentylzirconium hydride, bis(methylcyclopentadienyl)zirconium monochloride hydride, bis(indenyl)zirconium monochloride hydride, bis(cyclopentadienyl)zirconium dichloride, bis(cyclopentadienyl)zirconium dibromide, bis(cyclopentadienyl)methylzirconium monochloride, bis(cyclopentadienyl)ethylzirconium monochloride, bis(cyclopentadienyl)cyclohexylzirconium monochloride, bis(cyclopentadienyl)phenylzirconium monochloride, bis(cyclopentadienyl)benzyizirconium monochloride, bis(methylcyclopentadienyl)zirconium dichloride, bis(dimethylcyclopentadienyl)zirconium dichloride, bis(1-butylcyclopentadienyl)zirconium dichloride, bis(indenyl)zirconium dichloride, bis(indenyl)zirconium dibromide, bis(cyclopentadienyl)zirconium dimethyl, bis(cyclopentadienyl)zirconium diphenyl, bis(cyclopentadienyl)zirconium dibenzyl, bis(cyclopentadienyl)zirconium monomethoxymonochloride, bis(cyclopentadienyl)zirconium monoethoxymonochloride, bis(methylcyclopentadienyl)zirconium monoethoxymonochloride, bis(cyclopentadienyl)zirconium monophenoxymonochloride, and bis(fluorenyl)zirconium dichloride.

When M in the general formula (II) represents zirconium and the transitional metal compound includes at least two ligands with cycloalkadienyl skeleton that are joined to one another via a functional group including alkylene group such as ethylene and propylene, substituted alkylene group such as isopropylidene and diphenylmethylene, and substituted silylene group such as silylene and dimethylsilylene, specific examples of the transitional metal compound include ethylenebis(indenyl)dimethylzirconium, ethylenebis(indenyl)diethylzirconium, ethylenebis(indenyl)diphenylzirconium, ethylenebis(indenyl)methylzirconium monochloride, ethylenebis(indenyl)ethylzirconium monochloride, ethylenebis(indenyl)methylzirconium monobromide, ethylenebis(indenyl)zirconium dichloride, and ethylenebis(indenyl)zirconium bromide.

When polymerization is to be carried out in a homogenous system, these transitional metal compounds may be used either individually or, when it is desired to adjust the molecular weight distribution, in combinations of two or more compounds. Also, when solid catalysts are prepared in advance, the transitional metal compounds may be used either individually or, when it is desired to adjust the molecular weight distribution, in combinations of two or more compounds.

In the present invention, the fine particle carrier used in the preparation of a solid catalyst is a fine particle of inorganic compound sized 5 to 200 um. Examples of the inorganic compound for the fine particle carrier include oxides of $SiO_2$, $Al_2O_3$, $MgO$, and $TiO_2$, and mixtures thereof, with $SiO_2$ being most preferred. Organic compounds with reactive sites, such as hydroxyl group, to adsorb aluminoxane may also be used.

The fine particle carrier for use in the present invention typically includes surface hydroxyl group in an amount of 0.1 to 4 mmol/g and preferably in an amount of 1.0 to 3.0 mmol/g. The amount of the surface hydroxyl group can be readily determined by, for example, measuring the amount of methane generated when the fine particle carrier is exposed to trimethyl aluminum.

In the present invention, the amount of the modified methylaluminoxane preparation carried by the fine particle carrier can be generally controlled by the amount of surface hydroxyl group. Typically, the amount of the modified methylaluminoxane preparation carried by the solid catalyst is in the range of 3 to 10 mmol/g and preferably in the range of 4 to 8 mmol/g. As described above, the amount of surface hydroxyl group is measured by the amount of generated methane, which also includes methane generated by the reaction with water, alcohol or other compounds with active hydrogen that are adsorbed onto the fine particle carrier. However, as long as the amount of surface hydroxyl group as determined by the amount of methane, including methane generated by the reaction with adsorbed water, falls within the above-described range, the amount of the modified methylaluminoxane carried by the fine particle carrier remains within the range of 3 to 10 mmol/g.

The amount of the transitional metal compound carried by the particle carrier can be controlled by the shape of the particle carrier, the amount of surface hydroxyl group, and the amount of the modified methylaluminoxane preparation carried by the particle carrier. Typically, the amount of the transitional metal compound carried by the solid catalyst is in the range of 0.03 to 0.3 mmol/g and preferably in the range of 0.05 to 0.15 mmol/g. If the amount of the transitional metal compound carried by the solid catalyst is smaller than 0.03 mmol/g, the polymerization activity per 1 mole of the transitional metal compound tends to become high. Nevertheless, the polymerization activity per unit weight of the solid catalyst is significantly lowered, resulting in a reduced productivity of polymer and an increase in the cost required for preparing the solid catalyst. In comparison, if the amount of the transitional metal compound carried by the solid catalyst is larger than 0.3 mmol/g, then the activity per unit weight of the solid catalyst is reduced, as is the polymerization activity per 1 mole of the transitional metal compound. The cause of this phenomenon is believed to be that the transitional metal compound, when present on the surface of the particle carrier in excessive amounts, forms cluster-like deposits on the surface of the carrier. This interferes with the effective contact between the transitional metal compound and the modified methylaluminoxane co-catalyst, thereby leading to a reduced polymerization activity per unit weight of the solid catalyst.

The solid catalyst for olefin polymerization in accordance with the present invention can be prepared by bringing (A) transitional metal compound, (B) modified methylaluminoxane preparation, and solid carrier into contact with one another in a proper inert hydrocarbon solvent. While the solid catalyst for olefin polymerization in accordance with the present invention may be prepared using any proper method, it is most preferred to prepare it by first exposing the fine particle carrier to the modified methylaluminoxane in a solvent and then exposing the fine particle carrier to the transitional metal compound.

The olefin polymerization catalyst is typically prepared at temperatures of 0° C. to 200° C. and preferably at temperatures of 30° C. to 100° C.

The transitional metal compound and the modified methylaluminoxane preparation are typically kept in contact with the solid carrier for a time period of 0.5 to 10 hours and, preferably, for a time period of 0.5 to 2 hours.

Any inert hydrocarbon solvent may be used in the preparation of the olefin polymerization catalyst in accordance with the present invention. The hydrocarbon includes saturated aliphatic hydrocarbons such as n-pentane, n-hexane, n-heptane, n-octane, isooctane, and purified kerosines; cyclic aliphatic hydrocarbons such as cyclopentane, cyclohexane, methylcyclohexane, ethylcyclohexane, and cycloheptane; and aromatic hydrocarbons such as benzene, toluene, ethylbenzene, o-xylene, m-xylene, and p-xylene. Of these compounds, n-hexane, n-heptane, n-octane, cyclohexane, methylcyclohexane, and toluene are particularly preferred.

The modified methylaluminoxane preparation of the present invention can be used to promote polymerization in two different manners: it is used in a homogenous system or in a non-homogenous system in the form of catalyst carried by a carrier. Each manner of polymerization is suited to both the solution polymerization, which involves the use of solvents, and the bulk polymerization or the gas phase polymerization, neither of which involves solvents. Each of the two manners of polymerization utilizing the modified methylaluminoxane preparation of the present invention is also suitable for the continuous polymerization and the batch polymerization. In each case, hydrogen or other molecular weight-adjusting agents may optionally be used.

Various olefin monomers are used either individually or, for copolymerization, in combinations. Specific examples include α-olefins such as ethylene, propylene, 1-butene, 1-pentene, 1-hexene, 1-decene, 1-hexadecene, 1-octadecene, and 1-eicosene; halogen-substituted olefins such as difluoroethylene, trifluoroethylene, tetrafluoroethylene, and hexafluoropropene; and cyclic olefins such as cyclopentene, cyclohexene, and norbornene.

EXAMPLES

The present invention will now be described in detail with reference to several examples, which are only illustrative but not restrictive. In the processes described below, each reaction was carried out in nitrogen atmosphere and each solvent was dehydrated before use. Water used was ion-exchange water.

Example 1

(1) Synthesis of Modified Methylaluminoxane 315.2 g (1.59 mol %) triisobutyl aluminum (TIBAL) and 1219.2 g n-hexane were placed in a 5L separable flask equipped with a stirrer. To this solution, 20.1 g (1.11 mol) water was added at −5° C. To the resulting reaction mixture, 183.2 g (2.54 mol) trimethylaluminium (TMAL) was added and the mixture was heat-aged at 50° C. for 1 hour. Subsequently, 36.7 g (2.04 mol) water was added at the same temperature.

Additional 82.8 g (1.15 mol) TMAL was then added to the reaction mixture, and the mixture was heat-aged at 50° C. for the following 1 hour. To the resulting solution, 24.81 g (1.38 mol) water was added at −5° C. and the reaction mixture was heat-aged at 50° C. for additional 1 hour.

The resulting gel precipitate was removed by a glass filter to obtain an n-hexane solution of modified methylaluminoxane. In this solution, the yield as measured on the basis of aluminum atom was 80%. Shown in Table 1 are Me/iBu ratio determined by the gas chromatography performed on the gas generated upon hydrolysis of the modified methylaluminoxane; respective mole fractions of methyl group belonging to unreacted TMAL and modified methylaluminoxane preparation, as determined by $^1$H-NMR; and respective mole fractions of isobutyl group belonging to unreacted TIBAL and modified methylaluminoxane preparation, as determined by $^1$H-NMR.

(2) Evaluation of Ethylene Polymerization 250 ml toluene placed in a 500 ml four-necked flask equipped with a magnetic stirrer was heated to 34° C. To the flask, an n-hexane solution of 0.16 g (as measured on the basis of aluminum atom) modified methylaluminoxane was added, followed by the addition of bis (cycolpentadienyl) zirconium dichloride ($Cp_2ZrCl_2$) to a molar ratio of Al/Zr of 5000. Ethylene gas was then blown into the mixture while the mixture was maintained at 40° C. After 10 minutes, the supply of the gas was terminated and methanol was added to inactivate the catalyst. The resultant polyethylene was filtered and then dried. The polymerization activity of the product was determined to be $69 \times 10^6$ g·PE/mol·Zr·atm·hr.

Example 2

(1) Synthesis of Modified Methylaluminoxane Preparation

Modified methylaluminoxane was synthesized in the same manner as in Example 1, except that the second addition of water was added in an amount that gives a one-to-one ratio of water to TMAL. The results are shown in Table 1.

(2) Evaluation of Ethylene Polymerization

Evaluation was made in the same manner as in Example 1. The polymerization activity was determined to be $58\times10^6$ g·PE/mol·Zr·atm·hr.

Example 3

(1) Synthesis of Modified Methylaluminoxane Preparation

Modified methylaluminoxane was synthesized in the same manner as in Example 1, except that the amount of the second addition of TMAL was 114.6 g (1.59 mol). The results are shown in Table 1.

(2) Evaluation of Ethylene Polymerization

Evaluation was made in the same manner as in Example 1. The polymerization activity was determined to be $70\times10^6$ g·PE/mol·Zr·atm·hr.

Example 4

(1) Synthesis of Modified Methylaluminoxane 315.2 g (1.59 mol %) TIBAL and 1219.2 g n-hexane were placed in a 5L separable flask equipped with a stirrer. To this solution, 20.1 g (1.11 mol) water was added at $-5°$ C. To the resulting reaction mixture, 183.2 g (2.54 mol) TMAL was added and the mixture was heat-aged at $50°$ C. for 1 hour. Subsequently, 36.7 g (2.04 mol) water was added at the same temperature. The gel component was removed from the reaction mixture by a glass filter.

82.8 g (1.15 mol) TMAL was then added to the reaction mixture, and the mixture was heat-aged at $50°$ C. for the following 1 hour. To the resulting solution, 24.81 g (1.38 mol) water was added at $-5°$ C. and the reaction mixture was heat-aged at $50°$ C. for additional 1 hour.

The resulting gel precipitate was removed by a glass filter to obtain an n-hexane solution of modified methylaluminoxane. In this solution, the yield as measured on the basis of aluminum atom was 72%. Shown in Table 1 are Me/iBu ratio determined by the gas chromatography performed on the gas generated upon hydrolysis of the modified methylaluminoxane; respective mole fractions of methyl group belonging to unreacted TMAL and modified methylaluminoxane, as determined by $^1$H-NMR; and respective mole fractions of isobutyl group belonging to unreacted TIBAL and modified methylaluminoxane, as determined by $^1$H-NMR.

(2) Evaluation of Ethylene Polymerization

Evaluation was made in the same manner as in Example 1. The polymerization activity was determined to be $63\times10^6$ g·PE/mol·Zr·atm·hr.

Example 5

(1) Synthesis of Modified Methylaluminoxane 315.2 g (1.59 mol %) TIBAL and 1219.2 g n-hexane were placed in a 5L separable flask equipped with a stirrer. To this solution, 20.1 g (1.11 mol) water was added at $-5°$ C. To the resulting reaction mixture, 266 g (3.69 mol) TMAL was added and the mixture was heat-aged at $50°$ C. for 1 hour. Subsequently, 61.5 g (3.42 mol) water was added at the same temperature, and the mixture was heat-aged at $50°$ C. for additional 1 hour. The resulting gel precipitate was removed by a glass filter to obtain an n-hexane solution of modified methylaluminoxane preparation. In this solution, the yield as measured on the basis of aluminum atom was 79%. Shown in Table 1 are Me/iBu ratio determined by the gas chromatography performed on the gas generated upon hydrolysis of the modified methylaluminoxane preparation; respective mole fractions of methyl group belonging to unreacted TMAL and modified methylaluminoxane preparation, as determined by $^1$H-NMR; and respective mole fractions of isobutyl group belonging to unreacted TIBAL and modified methylaluminoxane preparation, as determined by $^1$H-NMR.

(2) Evaluation of Ethylene Polymerization

Evaluation was made in the same manner as in Example 1. The polymerization activity was determined to be $59\times10^6$ g·PE/mol·Zr·atm·hr.

Example 6

(1) Synthesis of Modified Methylaluminoxane

Modified methylaluminoxane was synthesized in the same manner as in Example 1, except that 583.0 g (1.59 mol) tri-n-octylaluminum was used in place of TIBAL. The results are shown in Table 1.

(2) Evaluation of Ethylene Polymerization

Evaluation was made in the same manner as in Example 1. The polymerization activity was determined to be $72\times10^6$ g·PE/mol·Zr·atm·hr.

Example 7

(1) Synthesis of Modified Methylaluminoxane

Modified methylaluminoxane was synthesized in the same manner as in Example 1, except that toluene was used in place of n-hexane solvent and the amount of the second addition of TMAL was 156.3 g (2.23 mol). The results are shown in Table 1.

(2) Evaluation of Ethylene Polymerization

Evaluation was made in the same manner as in Example 1. The polymerization activity was determined to be $73\times10^6$ g·PE/mol·Zr·atm·hr.

Comparative Example 1

(2) Evaluation of Ethylene Polymerization

Evaluation was made in the same manner as in Example 1, except that an n-hexane solution of a commercially available modified methylaluminoxane was used. Shown in Table 1 are Me/iBu ratio determined by the gas chromatography performed on the gas generated upon hydrolysis of the commercially available modified methylaluminoxane; respective mole fractions of methyl group belonging to unreacted TMAL and modified methylaluminoxane, as determined by $^1$H-NMR; and respective mole fractions of isobutyl group belonging to unreacted TIBAL and modified methylaluminoxane, as determined by 1H-NMR. The polymerization activity was determined to be $37\times10^6$ g·PE/mol·Zr·atm·hr.

Comparative Example 2

(1) Synthesis of Modified Methylaluminoxane 449.1 g (1.59 mol) tri-n-hexylaluminum (TNHAL) and 1219.2 g n-hexane were placed in a 5L separable flask equipped with a stirrer. To this solution, 20.1 g (1.11 mol) water was added at $-5°$ C. To the resulting reaction mixture, 183.2 g (2.54 mol) TMAL was added and the mixture was heat-aged at $50°$ C. for 1 hour. Subsequently, 36.7 g (2.04 mol) water was added at the same temperature. The reaction mixture was heat-aged at $50°$ C. for additional 1 hour.

The resulting solid precipitate was removed by a glass filter to obtain a solution of modified methylaluminoxane. In this solution, the yield as measured on the basis of aluminum atom was 75%. Shown in Table 1 are Me/n-Hex ratio determined by the gas chromatography performed on the gas generated upon hydrolysis of the modified methylaluminoxane; respective mole fractions of methyl group belonging to unreacted TMAL and modified methylaluminoxane, as determined by $^1$H-NMR; and respective mole fractions of n-hexyl group belonging to unreacted TNHAL and modified methylaluminoxane, as determined by $^1$H-NMR.

(2) Evaluation of Ethylene Polymerization

Evaluation was made in the same manner as in Example 1. The polymerization activity was determined to be 7×10 g·PE/mol·Zr·atm·hr.

Comparative Example 3

(2) Evaluation of Ethylene Polymerization

Evaluation of ethylene polymerization was made in the same manner as in Example 1, except that commercially available polymethylaluminoxane was used in place of modified methylaluminoxane. The mole fractions of methyl group belonging to unreacted TMAL and polymethylaluminoxane as determined by $^1$H-NMR were 47.7 mol % (Me (TMAL)) and 52.3 mol % (Me(PMAO)), respectively. The polymerization activity was determined to be 62×10$^6$ g·PE/mol·Zr·atm·hr.

Comparative Example 4

Methylaluminoxane component was synthesized in the same manner as in Example 12 described in Japanese Patent Laid-Open Publication No. 2000-119279: Under nitrogen atmosphere, 40 g of a 25% toluene solution of TIBAL (0.050 mol TIBAL) was placed in a completely dried 100 ml flask replaced with nitrogen. The 100 ml flask was equipped with a magnetic stirrer and a resistance thermometer for measuring the temperature of the reaction mixture. 1.099 g (0.061 mol) water was added at a reaction temperature of 0 to 10° C. while the mixture was being stirred. Subsequently, the reaction mixture was heated to 75° C. to cause a viscous gel-like material to form. 3.63 g (0.050 mol) TMAL was then added to the reaction mixture, and reaction was allowed to proceed at 80° C. for 1 hour. A gel-like insoluble material was formed in the resulting reaction mixture. The aluminum concentration in the supernatant of the reaction mixture was 3.51 wt %. The yield as measured on the basis of aluminum atom was determined to be 58.9%. Shown in Table 1 are Me/iBu ratio determined by the gas chromatography on the gas generated from the resulting supernatant upon hydrolysis; respective mole fractions of methyl group belonging to unreacted TMAL and modified methylaluminoxane preparation, as determined by $^1$H-NMR; and respective mole fractions of isobutyl group belonging to unreacted TIBAL and modified methylaluminoxane preparation, as determined by $^1$H-NMR.

(2) Evaluation of Ethylene Polymerization

Evaluation was made in the same manner as in Example 1. The polymer was obtained in trace amounts.

Comparative Example 5

Methylaluminoxane component was synthesized in the same manner as in Comparative Example 4, except that n-hexane was used as a solvent. The yield of aluminum was determined to be 94.8%. The Me/iBu ratio determined by the gas chromatography on the gas generated from the resulting supernatant upon hydrolysis is shown in Table 1, along with the respective mole fractions of methyl group belonging to unreacted TMAL and modified methylaluminoxane preparation as determined by $^1$H-NMR; and respective mole fractions of isobutyl group belonging to unreacted TIBAL and modified methylaluminoxane preparation as determined by $^1$H-NMR.

(2) Evaluation of Ethylene Polymerization

Evaluation was made in the same manner as in Example 1. The polymerization activity of the product was determined to be 8×10$^6$ g·PE/mol·Zr·atm·hr.

TABLE 1

|  | Yield (%) | Me/R | PE activity *10$^6$ g/mol-Zr · atm · hr | Me (MMAO) (mol %) | Me (TMAL) (mol %) | R (MMAO) (mol %) | R (AlR$_3$) (mol %) |
|---|---|---|---|---|---|---|---|
| Example 1 | 80 | 4.8 | 69 | 75.9 | 7.0 | 13.5 | 3.6 |
| Example 2 | 84 | 4.7 | 58 | 70.8 | 11.7 | 11.5 | 6.0 |
| Example 3 | 75 | 5.8 | 70 | 82.0 | 2.9 | 10.1 | 5.0 |
| Example 4 | 72 | 5.1 | 63 | 75.0 | 8.5 | 13.0 | 3.5 |
| Example 5 | 79 | 3.6 | 55 | 70.0 | 8.0 | 14.8 | 7.2 |
| Example 6 | 80 | 6.7 | 72 | 87.0 | 3.5 | 6.5 | 7.0 |
| Example 7 | 88 | 13.1 | 73 | 90.0 | 2.9 | 5.1 | 2.0 |
| Comparative Example 1 | 85 | 2.7 | 37 | 58.0 | 14.6 | 14.7 | 12.7 |
| Comparative Example 2 | 75 | 2.8 | 7 | 38.5 | 28.7 | 15.5 | 17.4 |
| Comparative Example 4 | 58.9 | 1.6 | trace | 0 | 62.1 | 9.2 | 28.7 |
| Comparative Example 5 | 94.8 | 4.2 | 8 | 10.8 | 69.8 | 12.9 | 6.5 |

MMAO: modified methylaluminoxane
Examples 1–5, 7, and Comparative Examples 1, 4, and 5: R = isobutyl group,
Example 6: R = n-octyl group
Comparative Example 2: R = n-hexyl group Example 8

(2) Preparation of Catalyst Carried by Silica 7 g silica (specific surface area=292 m$^2$/g; the amount of surface hydroxyl group=3.2 mmol/g; average particle size= 42 μm) and 200 ml toluene were placed in a completely dried glass flask replaced with nitrogen to form a suspension. At room temperature, 80 mmol modified methylaluminoxane preparation of Example 1 was added dropwise to the suspension over 30 minutes. The solution was then heated to 80° C. and aged at this temperature for 1 hour. The supernatant was removed and the residue was washed with toluene to obtain a solid silica carrying modified methylaluminoxane.

At room temperature, 0.55 mmol zirconocene dichloride in toluene was added dropwise to the solid slurry catalyst obtained above and the mixture was aged at the temperature for 2 hours. Following removal of the supernatant, the residue was washed with dried toluene to obtain a solid catalyst containing 0.090 mmol Zr and 4.95 mmol Al per 1 g of the catalyst.

(3) Evaluation of Ethylene Polymerization 500 ml hexane was placed in a 1000 ml autoclave equipped with a magnetic stirrer and the atmosphere in the reaction system was replaced with ethylene. The system was then heated to 70° C. 0.89 mmol TIBAL and then 20 mg of the above-prepared solid catalyst were added to the system and polymerization was carried out under ethylene pressure of 0.78 Mpa for 30 minutes. The resultant polymer was collected by filtration and was then dried at 60° C. for 6 hours under reduced pressure to obtain polyethylene. The activity of the catalyst to catalyze polymerization of ethylene was determined to be 720 kg·PE/mol·Zr·atm·hr. Upon polymerization, the polymer was not deposited on the walls of the polymerization container or on the blades of the stirrer.

Example 9

(2) Preparation of Catalyst Carried by Silica

A solid catalyst was prepared in the same manner as in Example 8, except that the modified methylaluminoxane obtained in Example 2 was used. The solid catalyst contained 0.093 mmol Zr and 5.65 mmol Al per 1 g of the catalyst.

(3) Evaluation of Ethylene Polymerization

Polymerization of ethylene was carried out in the same manner as in Example 8, except that the solid catalyst prepared above was used. The polymerization activity was determined to be 662 kg·PE/mol·Zr·atm·hr. Upon polymerization, the polymer was not deposited on the walls of the polymerization container or on the blades of the stirrer.

Example 10

(1) Synthesis of Modified Methylaluminoxane Preparation 50.0 g (0.25 mol) TIBAL and 1200 g toluene were placed in a 5L separable flask equipped with a stirrer. At −5° C., 1.4 g (0.07 mol) water was added dropwise to the solution. 180.0 g (2.50 mol) TMAL was then added to the reaction mixture and the mixture was heat-aged at 50° C. for 1 hour. 33.8 g (1.88 mol) water was then added to the mixture at this temperature. The mixture was subsequently heat-aged at 50° C. for additional 1 hour.

The resulting solid precipitate was removed by a glass filter to obtain a modified methylaluminoxane solution. In this solution, the yield as measured on the basis of aluminum atom was 86%. The Me/iBu ratio determined by the gas chromatography performed on the gas generated upon hydrolysis of the modified methylaluminoxane is shown in Table 2, along with the respective mole fractions of methyl group belonging to unreacted TMAL and modified methylaluminoxane preparation as determined by $^1$H-NMR; and the respective mole fractions of isobutyl group belonging to unreacted TIBAL and modified methylaluminoxane preparation as determined by $^1$H-NMR.

(2) Preparation of Catalyst Carried by Silica

A solid catalyst was prepared in the same manner as in Example 8, except that the modified methylaluminoxane obtained above was used. The solid catalyst contained 0.07 mmol Zr and 5.95 mmol Al per 1 g of the catalyst.

(3) Evaluation of Ethylene Polymerization

Polymerization of ethylene was carried out in the same manner as in Example 8, except that the solid catalyst prepared above was used. The polymerization activity was determined to be 770 kg·PE/mol·Zr·atm·hr. Upon polymerization, the polymer was not deposited on the walls of the polymerization container or on the blades of the stirrer.

Comparative Example 6

(2) Preparation of Catalyst Carried by Silica

A solid catalyst was prepared in the same manner as in Example 8, except that the hexane solution of the commercially available modified methylaluminoxane used in Comparative Example 1 was used. The solid catalyst contained 0.087 mmol Zr and 5.80 mmol Al per 1 g of the catalyst.

(3) Evaluation of Ethylene Polymerization

Polymerization of ethylene was carried out in the same manner as in Example 8, except that the solid catalyst prepared above was used. The polymerization activity was determined to be 357 kg·PE/mol·Zr·atm·hr. Upon polymerization, the polymer was not deposited on the walls of the polymerization container or on the blades of the stirrer.

Comparative Example 7

(2) Preparation of Catalyst Carried by Silica A solid catalyst was prepared in the same manner as in Example 8, except that a toluene solution of a commercially available modified methylaluminoxane was used. The respective mole fractions of methyl group belonging to unreacted TMAL and modified methylaluminoxane as determined by $^1$H-NMR are shown in Table 2, along with the respective mole fractions of isobutyl group belonging to unreacted TIBAL and modified methylaluminoxane as determined by $^1$H-NMR. The resultant solid catalyst contained 0.080 mmol Zr and 4.80 mmol Al per 1 g of the catalyst.

(3) Evaluation of Ethylene Polymerization

Polymerization of ethylene was carried out in the same manner as in Example 8, except that the solid catalyst prepared above was used. The polymerization activity was determined to be 189 kg·PE/mol·Zr·atm·hr. Upon polymerization, the polymer was not deposited on the walls of the polymerization container or on the blades of the stirrer.

Comparative Example 8

(2) Preparation of Catalyst Carried by Silica

A solid catalyst was prepared in the same manner as in Example 8, except that the commercially available polymethylaluminoxane used in Comparative Example 3 was used. The solid catalyst contained 0.068 mmol Zr and 4.56 mmol Al per 1 g of the catalyst.

(3) Evaluation of Ethylene Polymerization

Polymerization of ethylene was carried out in the same manner as in Example 8, except that the solid catalyst prepared above was used. The polymerization activity was determined to be 323 kg·PE/mol·Zr·atm·hr. Upon polymerization, the polymer was not deposited on the walls of the polymerization container or on the blades of the stirrer.

Comparative Example 9

(2) Preparation of Catalyst Carried by Silica

A solid catalyst was prepared in the same manner as in Example 8, except that a concentrated polymethylaluminoxane was used that was prepared by concentrating the commercially available PMAO used in Comparative Example 3 under reduced pressure. The mole fractions of methyl group belonging to unreacted TMAL and polymethylaluminoxane as determined by $^1$H-NMR of the concentrated polymethylaluminoxane were 68.7 mol % (Me(PMAO)) and 31.3 mol % (Me(TMAL)), respectively. The resultant solid catalyst contained 0.084 mmol Zr and 5.43 mmol Al per 1 g of the catalyst.

(3) Evaluation of Ethylene Polymerization

Polymerization of ethylene was carried out in the same manner as in Example 8, except that the solid catalyst prepared above was used. The activity of the catalyst to catalyze polymerization of ethylene was determined to be 492 kg·PE/mol·Zr·atm·hr. Upon polymerization, the polymer was not deposited on the walls of the polymerization container or on the blades of the stirrer.

TABLE 2

|  | Yield (%) | Me (MMAO) (mol %) | Me (TMAL) (mol %) | iBu (MMAO) (mol %) | iBu (TIBAL) (mol %) |
|---|---|---|---|---|---|
| Example 10 | 75 | 66.8 | 28.0 | 1.8 | 3.5 |
| Comparative Example 7 | 90 | 61.7 | 5.8 | 24.1 | 8.4 |

MMAO: modified methylaluminoxane

The modified methylaluminoxane preparation in accordance with the present invention is advantageous in that a large proportion of methyl groups present in the preparation belongs to aluminoxane while the preparation contains a small proportion of alkyl groups other than methyl groups belonging to aluminoxane. An olefin polymerization catalyst prepared in the form of a combination of the modified methylaluminoxane preparation and a transitional metal compound stably exhibits a high polymerization activity.

What is claimed is:

1. A method for producing a modified methylaluminoxane preparation which comprises hydrolyzing a) an organoaluminum compound represented by the following formula (I):

$$R^1_m AlX_{3-m} \qquad (I)$$

wherein $R^1$ represents a straight-chained or branched hydrocarbon group selected from the group consisting of alkyl, alkenyl, and aryl groups having 2 to 20 carbon atoms; X represents a hydrogen atom, halogen atom, alkoxy group, or allyloxy group; and $0 < m \leqq 3$ with b) trimethyl aluminum,
by adding said trimethyl aluminum to said organoaluminum compound of formula (I) in the presence of water; and repeating the step of adding said trimethyl aluminum as many times as necessary,
whereby in said modified inethylaluminoxane, a mole fraction of methyl group of the modified aluminoxane unit with respect to a total number of moles of the hydrocarbon group having 2 to 20 carbon atoms and methyl group present in the modified methylaluminoxane preparation is 65% or greater.

2. The method of claim 1 wherein the organoaluminum compound of formula (I) is at least one selected from the group consisting of triisobutyl aluminum, tri-n-hexylaluminum and tri-n-octylaluminum.

* * * * *